(12) United States Patent
Dinesen et al.

(10) Patent No.: US 11,272,876 B2
(45) Date of Patent: Mar. 15, 2022

(54) MULITFACTORIAL TELEHEALTH CARE PREGNANCY AND BIRTH MONITORING

(71) Applicant: Viewcare Technologies 1 ApS, Herlev (DK)

(72) Inventors: Birthe Irene Dinesen, Aalborg (DK); Diana Kjaer Thing Riknagel, Gedsted (DK); Johannes Jan Stujik, Terndrup (DK)

(73) Assignee: Viewcare Technologies 1 ApS, Herlev (DK)

( * ) Notice: Subject to any disclaimer, the term of this patent is extended or adjusted under 35 U.S.C. 154(b) by 18 days.

(21) Appl. No.: 16/375,632

(22) Filed: Apr. 4, 2019

(65) Prior Publication Data

US 2019/0231248 A1 Aug. 1, 2019

Related U.S. Application Data

(63) Continuation of application No. 14/361,690, filed as application No. PCT/DK2012/050439 on Nov. 30, 2012, now Pat. No. 10,278,635.

(30) Foreign Application Priority Data

Dec. 1, 2011 (EP) .................................. 11191475

(51) Int. Cl.
*A61B 5/38* (2021.01)
*A61B 5/00* (2006.01)
(Continued)

(52) U.S. Cl.
CPC ............ *A61B 5/4343* (2013.01); *A61B 5/389* (2021.01); *A61B 7/00* (2013.01); *A61B 5/0011* (2013.01);
(Continued)

(58) Field of Classification Search
CPC . A61B 5/4362; A61B 5/4343; A61B 5/02411; A61B 8/06; A61B 8/0866
See application file for complete search history.

(56) References Cited

U.S. PATENT DOCUMENTS 4,781,200 A 11/1988 Baker
5,749,831 A * 5/1998 Baker ...................... A61B 8/02
600/301

(Continued)

FOREIGN PATENT DOCUMENTS

CN 1266725 A 9/2000
WO 98/58582 A1 12/1998
(Continued)

OTHER PUBLICATIONS

International Search Report dated May 7, 2013, issued in corresponding International Application No. PCT/DK2012/050439, filed Nov. 30, 2012, 5 pages.

(Continued)

*Primary Examiner* — Michael J D'Abreu
(74) *Attorney, Agent, or Firm* — Christensen O'Connor Johnson Kindness PLLC

(57) ABSTRACT

A system for monitoring a fetus in a pregnant woman, and/or the maternal health risk for pregnancies complicated by such as pre-eclampsia and hypertensive disorders is configured to be worn by the pregnant woman, preferably so as to allow monitoring during daily life, e.g. in the form of an adhesive patch. The unit has a sound sensor, e.g. a microphone or accelerometer, to be positioned on the skin of the abdominal area so as to detect a vascular sound from umbilical arteries of the fetus or from the uterine arteries of the pregnant woman. The sound sensor is functionally connected to a processing unit which executes a processing algorithm on the captured vascular sound and extracts a signal parameter accordingly. The processing unit then communicates the (Continued)

signal parameter, e.g. using an audio signal, a visual display or by means of a wired or a wireless data signal.

18 Claims, 3 Drawing Sheets

(51) Int. Cl.
    *A61B 7/00*     (2006.01)
    *A61B 5/389*     (2021.01)
    *A61B 5/026*     (2006.01)

(52) U.S. Cl.
    CPC ........... *A61B 5/026* (2013.01); *A61B 2503/02* (2013.01); *A61B 2562/02* (2013.01)

(56) References Cited

U.S. PATENT DOCUMENTS

| | | |
|---|---|---|
| 5,817,035 A | 10/1998 | Sullivan |
| 6,024,701 A | 2/2000 | Almog |
| 6,171,263 B1 | 1/2001 | Sullivan |
| 6,340,346 B1 | 1/2002 | Almog et al. |
| 9,351,682 B2 | 5/2016 | Euliano, II et al. |
| 2004/0073094 A1 | 4/2004 | Baker |
| 2005/0065439 A1* | 3/2005 | Fernando ............... G01S 15/58 600/454 |
| 2005/0267377 A1 | 12/2005 | Marossero et al. |
| 2005/0277841 A1 | 12/2005 | Shennib |
| 2007/0260155 A1 | 11/2007 | Rapoport |
| 2009/0143650 A1 | 6/2009 | Guion-Johnson et al. |
| 2011/0306862 A1 | 12/2011 | Hayes-Gill et al. |
| 2012/0065479 A1 | 3/2012 | Lahiji et al. |
| 2012/0083699 A1 | 4/2012 | Reuter et al. |
| 2012/0179046 A1 | 7/2012 | Kabakov et al. |
| 2012/0232398 A1 | 9/2012 | Roham et al. |

FOREIGN PATENT DOCUMENTS

| | | |
|---|---|---|
| WO | 2008/000254 A1 | 1/2006 |
| WO | 2011/063077 A1 | 5/2011 |
| WO | 2011/137930 A1 | 11/2011 |

OTHER PUBLICATIONS

Extended European Search Report dated Jun. 11, 2021, issued in corresponding European Application No. EP 21159952.7, 8 pages.

* cited by examiner

Time (s)

MULITFACTORIAL TELEHEALTH CARE PREGNANCY AND BIRTH MONITORING

CROSS-REFERENCE TO RELATED APPLICATIONS

This application is a continuation of U.S. application Ser. No. 14/361,690, filed May 29, 2014, which is a National stage of International Patent Application No. PCT/DK2012/050439, filed Nov. 30, 2012, which is based on European Patent Application No. 11191475.0, filed Dec. 1, 2011. Each application is incorporated herein by reference in its entirety.

FIELD OF THE INVENTION

The present invention relates to field of medical devices, more specifically such as telehealth care systems and pregnancy and birth monitoring equipment. Especially, the invention provides a method and system for monitoring a fetus in the uterus of a pregnant women by monitoring the state of the blood flow between the fetus and the placenta by means of detecting blood flow in the umbilical arteries and/or by monitoring the state of the perfusion of the uterus by detecting blood flow in the uterine arteries.

BACKGROUND OF THE INVENTION

Caretaking of pregnant women in the group at risk for premature birth continues to be a huge clinical challenge being one of the main reasons for neonatal morbidity and mortality.

In the clinic, the growth of the fetus is normally estimated based on a simple distance measure of the pregnant woman's abdomen. This only provides a rough measure of the growth of the fetus, and in case any abnormal development is detected, the fetus has most likely suffered from an abnormal development during several weeks before it is detected.

Once the pregnant woman is categorized as belonging to the high risk group for impaired growth other methods exist for monitoring the development of the fetus. A sufficient blood flow to the uterus and between the fetus and the placenta is vital for the fetus to develop. Thus, detection of any abnormal blood flow in the uterine arteries and the umbilical arteries is important with respect to monitoring the state of the fetus. This is possible by means of Doppler measurements, using ultrasound scanning equipment, to examine arterial blood flow. Hereby, e.g. the Pulsatility Index (PI) can be determined, and thus compared to a tabulated threshold value in order to assist the medical staff at the clinic in determining if the blood supply to the fetus is normal or if any action is required. Ultrasound scanning for determination of uterine and umbilical arterial blood flow is used in cases such as: Intra Uterine Growth Restriction (IUGR), twin pregnancy, maternal hypertension, maternal pre-eclampsia, maternal diabetes, and women pregnant after In Vitro Fertilization (IVF).

Many women, being categorized as belonging to the high risk group, become anxious and many of those women either contact the clinic or hospital at regular intervals to ask for examination, and many women are finally hospitalized, e.g. during weeks, in spite the fact that their fetus has a normal development. Thus, there is a need for a solution to allow this group of woman to be monitored more closely during at least a part of their pregnancy without the need for hospitalization.

For pregnant women diagnosed with such as pre-eclampsia or hypertensive disorders the feto-placental circulation is affected as the maternal state of pre-eclampsia or hypertension worsens, therefore there is a need for a system to monitor the maternal health risk during pregnancy.

SUMMARY OF THE INVENTION

Following the above description, it may be seen as an object of the present invention to provide a system for monitoring a fetus in a pregnant woman and the maternal health risk for pregnancies complicated by such as pre-eclampsia and hypertensive disorders which is suitable for low-cost implementation and more continuously monitoring without the need for skilled personnel to perform an examination.

In a first aspect, the invention provides a system for monitoring a pregnant woman or a fetus in a pregnant woman, and/or the maternal health risk for pregnancies complicated by such as pre-eclampsia and hypertensive disorders. The system comprises a portable unit arranged to be carried by the pregnant woman, the portable unit comprising at least one sound sensor arranged for being positioned on the skin of the abdominal area and arranged to detect a vascular sound from a uterine artery or from an umbilical artery of a fetus present in the pregnant woman's uterus and to generate a first signal accordingly, and a processing unit functionally connected to receive the first signal, wherein the processing unit is arranged to execute a first processing algorithm on the first signal so as to extract at least a first signal parameter accordingly, and wherein the processing unit is arranged to communicate the at least first signal parameter.

Such system is suitable for monitoring the maternal vasculatory state in relation to the pregnancy, and thus the system can serve to monitor the health state of the pregnant woman as well as the fetus. The system is advantageous since the portable or wearable unit, e.g. in the form of an adhesive patch, can be worn by the pregnant woman during several hours, days or even weeks, where the vascular sounds from the uterine arteries or the umbilical arteries can be continuously monitored or at least monitored at regular intervals. The processing unit can be integrated in the wearable unit, e.g. within an adhesive patch, or the processing unit can be constituted by a separate device worn in a belt or the like. Certain embodiments can serve as a monitor system to be worn in daily life, and during the birth phase, the system can eliminate or at least partly replace existing monitoring systems.

The system can also be used to provide an early diagnosis of pregnancy toxaemia.

The invention is based on the insight, that it is possible to detect vascular sound from the uterine arteries and the umbilical arteries by using a sound sensor in the form of a microphone or an accelerometer to capture sound in the such as in the frequency range 50-5000 Hz on the skin of the abdominal area of the pregnant woman. Compared to the much more complicated Doppler ultrasound equipment, it is possible to provide a system with at least the sound sensor in a portable or wearable unit so as to allow continuous monitoring of at least one parameter related to the blood flow in the uterine arteries or the umbilical arteries. In practice, Doppler ultrasound measurement of blood flow cannot be performed without skilled persons being present and thus cannot be performed without the pregnant woman being present at a clinic or at a hospital. Even if not performed often, it may be argued that the ultrasound signals constitute a health risk for the fetus, whereas sound recording on the surface of the skin can be performed very often, e.g. continuously, without any health risk.

With the system, the pregnant woman can be monitored while living a normal life at home and still having the feeling that she is taken care of, since the system can immediately give an alarm in case any abnormality in the blood flow is detected. The processing unit itself may be capable of triggering an alarm based on the at least first signal parameter, e.g. a calculated Pulsatility Index (PI), which is compared to a tabulated threshold value and which is considered to be outside a normal range. For example, the processing unit may itself have an acoustic or visual or vibrator alarm, or the processing unit may send a message to the pregnant woman's mobile phone.

In some tele-healthcare embodiments, the processing unit communicates the at least first parameter, e.g. PI, via e.g. a home Personal Computer via the internet to a server at the hospital. Hereby, the medical staff at the hospital can monitor vital data for the patient continuously or at regular intervals, and e.g. the history of vital parameters may be tracked and stored for later use. Hereby, it is possible to quickly detect any abnormality at an early state, which significantly improves the chance of successful treatment without either the fetus or the pregnant woman suffering.

Still further, the system is advantageous also for the pregnant woman to wear during the birth phase, where the uterine arterial blood flow and the umbilical arterial blood flow provide additional knowledge regarding the health status of the fetus. Especially, in embodiments including also EMG as well as fetal ECG sensors integrated in an adhesive patch to be placed on the abdominal area of the pregnant woman. Thus, the most vital parameters in the birth phase can be monitored in an easy way without the need for any additional sensor equipment, and especially invasive electrodes on the fetus may be avoided. Further, the system is advantageous for the pregnant woman to wear during surgery, especially during caesarean section. Thus, there is no need for additional technology to monitor the fetal condition during such surgery.

In one embodiment, the wearable unit further comprises at least one sensor arranged to detect an electromyographic (EMG) activity of the pregnant woman's uterus and to generate a second signal accordingly, and wherein the processing unit is functionally connected to receive the second signal. Such EMG sensor is advantageous for monitoring any abnormal pre term myometrial activity in the uterus during the pregnancy at an early stage, so as to be able to intervene and possibly avoid pre term birth. However, the EMG sensor is also advantageous in the birth phase, where the myometrial activity in the uterus is important for determining the intrapartal status.

In one embodiment, the wearable unit further comprises at least one sensor (S3) arranged to detect an electrocardiographic (ECG) signal from the fetus in the pregnant woman's uterus and to generate a third signal accordingly, and wherein the processing unit is functionally connected to receive the third signal. Hereby it is possible to monitor for abnormalities in the ECG of the fetus which can be used to monitor the health state of the fetus in the pre-birth phase and during the birth phase, e.g. by monitoring pulse rate in order to detect any tachycardia or bradycardia. Further, knowledge of the fetal ECG also allows monitoring of other parameters of the fetal ECG, such as monitoring of the ST segment in order to detect possible ST elevation.

In a preferred embodiment, the wearable unit comprises both the sound sensor, an EMG sensor and an ECG sensor, as just described. Especially, all of the mentioned three sensors may be placed within an adhesive patch. Preferably, the processing unit is arranged to process all of the first signal, the second signal and the third signal and to generate a combined signal parameter in response to all of the first, second and third signals. Hereby, a combined measure or status of the health condition of the fetus is possible, and it is possible to generate an alarm in case abnormalities are detected.

In general, the portable or wearable unit may comprise an adhesive patch within which the at least one sound sensor is arranged so as to allow the sound sensor to be in contact with the skin of the abdominal area of the pregnant woman. Especially, the adhesive patch may have a semi-circular shape and be suited for being positioned on the skin of the abdominal area of the pregnant woman, medially from the umbilicus. However, the portable or wearable unit in which the sound sensor is placed may alternatively be in the form of a small device arranged for positioning on the abdominal area of the pregnant woman by means of a strap, a belt or a plaster etc.

In some embodiments, the system comprises two or more adhesive patches arranged for position on respective areas of the abdomen of the pregnant woman, wherein each adhesive patch has at least one sound sensor arranged therein which is functionally connected to the processing unit. Such embodiments are advantageous, since sensor patches can be positioned at several positions, e.g. on both sides of the abdominal area, so as to be able to capture uterine or umbilical artery sound independent of the actual position of the fetus.

The portable or wearable unit may comprise a plurality, e.g. two, three or even more sound sensors arranged at different positions, e.g. within an adhesive patch or several adhesive patches, so as to provide a better chance of catching the vascular sound from the uterine arteries and the umbilical arteries independently of the position of the fetus. Hereby, the processing unit may be arranged to compare the quality of the sound signals from the plurality of sensors to process the signal from the sound sensor providing the highest quality of vascular sound.

Furthermore, each sound sensor may be accompanied by an additional microphone, a "room microphone", where the sound sensor is recording the sound from within the abdominal wall and the additional microphone is located so as to record sound from the environment. Preferably, the processing unit is then arranged to perform adaptive filtering of the signal from the sound sensor and thereby eliminate noise from the surroundings in the signal which is further processed. Especially, such noise cancellation processing may be based on a noise cancellation algorithm comprising Wiener-filtering. With a "room microphone" and suitable noise cancellation processing, it is possible to obtain a more precise result of the processing, and it is possible to detect the rather weak sound or accelerometer signals and thus perform the monitoring even in environments with a significant noise level, such as in the traffic or the like.

The processing unit may form part of the portable or wearable unit. E.g. the processing unit may be arranged within an adhesive patch, especially within the same patch in which the sound sensor is also placed. The sound sensor, the necessary analog electronic circuits, analog-to-digital converter, a processor running the first processing algorithm, and a battery arrangement to drive all of these elements, may be arranged within the adhesive patch. The processing unit within the patch may then be able to communicate the first signal parameter and possibly more data to an external device, e.g. a mobile phone etc. via a wire or wirelessly using e.g. Bluetooth technology or the like.

Alternatively, the processing unit may be implemented as one of: a portable device, such as a mobile phone, a Personal Computer, and a server system. In such systems, the first signal from the sound sensor is preferably analog-to-digitally converted and transmitted by wire or wirelessly in data packets to the external device which then executes the first processing algorithm on the data packets and generates the first signal parameter. Especially, the portable device may be a small battery driven device arranged for being worn by the pregnant woman in a belt or a strap or in a pocket. However, the external device may also be a smart phone with the first processing algorithm implemented as an application to be run on the smart phone.

In some embodiments a smart phone, or a similar device, with a suitable application, is arranged to receive data from the portable unit by means of a short-range wireless communication e.g. Bluetooth, or the like. Thus, in such embodiments, the portable unit, e.g. in the form of an adhesive patch, only needs to include the necessary electronic means arranged for receiving signals from the sensors, e.g. microphone and possibly other sensors, and to communicate those signals to the smart phone via the short-range wireless communication link. The smart phone application serves to perform the entire first processing algorithm, thus utilizing the processing power in the smart phone, thereby allowing the processing capabilities in the portable or wearable unit to be limited, thereby allowing a low cost and low power processor to be used. However, it is to be understood that several possibilities for the structure of the data to be communicated between the portable or wearable unit and the smart phone. To reduce the amount of data to be communicated to the smart phone, part of or even all of the first processing algorithm may be performed by processing circuit included in the portable or wearable unit. The smart phone can be used for the communication of the signal parameter to the pregnant woman by means of audio and/or video signals. However, the portable or wearable unit may also include audible and/or video means arranged to provide the woman and/or a health care practitioner with the result of the monitoring, e.g. in the form of an audible or visible warning, if an abnormal situation is detected.

In some embodiments, the portable unit collects data from the sound sensor for a period of time, e.g. several hours or one or more days. These data are then transferred to another device in which the processing unit is implemented, e.g. a Personal Computer or the like, e.g. by data transfer from the portable unit via a USB interface or the like.

The sound sensor may be a sound sensor as known within the art of electronic stethoscopes for sensing heart and lung sounds, e.g. as an example of a specific product: 3M Littman® Electronic Stethoscope Model 4000. Other type of microphones could be used, however it is preferred that the sound sensor used has a low noise floor, preferably a noise floor which is below 40 dB Sound Pressure Level (SPL, i.e. sound pressure level re. 20 µPa), more preferably below 30 dB SPL, more preferably below 25 dB SPL. The sound sensor is preferably suited to cover at least the frequency range 100-1000 Hz, more preferably 50-5000 Hz. It is preferred that the microphone is shaped and suited for and fixed to the woman, so as to be in close contact with the abdominal skin. As mentioned, the sound sensor can be in the form of an accelerometer as an alternative or in addition to a microphone.

In preferred embodiments, the first processing algorithm is arranged to band-pass filter the first signal and generate a band-pass filtered first signal accordingly. The band-pass filter may have a bandwidth within 50-5000 Hz. The lower cut-off frequency of the band-pass filter may be within the range 30-200, preferably within 50-150 Hz, or within 50-100 Hz. The upper cut-off frequency may be within the range 800-20000 Hz, preferably within 1000-10000 Hz, such as within 1500-5000 Hz. In special embodiments, the band-pass filter may have a bandwidth of such as 50-4000 Hz, or 50-3000 Hz, or 80-2000 Hz, or 100-1000 Hz, or 200-800 Hz. It is to be understood that the entire band-pass filtering effect or at least a part of it may be provided by the acoustical and/or mechanical design of the sound sensor. Thus, it may be preferred to use a specially designed sound sensor with a frequency characteristics serving to suppress sound outside the most important frequency range, which may eliminate or at least supplement the need for a band-pass filter as part of the processing.

Subsequently, the first processing algorithm is preferably arranged to detect a signal envelope, such as by rectifying the band-pass filtered first signal and to generate a rectified first signal accordingly. Subsequently, the first processing algorithm is preferably further arranged to low-pass filter the rectified first signal and to generate a low-pass filtered first signal accordingly. The low-pass filter may have a cut-off frequency within the interval 1-20 Hz, such as within the interval 2-15 Hz, such as within the interval 3-10 Hz, such as within the interval 4-8 Hz. Subsequently, the first processing algorithm is preferably arranged to extract a first signal parameter comprising at least one of: a Pulsatility Index, a rise time of the sound from the arteries, and a decay time of sound from the arteries, venous flow, and closure timing of the aortic valve, thereby the end of systole and the start of the diastole. An intermediate step of providing a signal envelope may be performed before the step of extracting the first signal parameter.

It is to be understood that alternative signal processing algorithms may be performed on the signals from the sound sensor to derive signal parameters related to the uterine arterial blood flow or the umbilical arterial blood flow.

In some embodiments, the processing unit is arranged to perform an algorithm serving to process recorded sound from the sound sensor with the purpose of determining if the recorded sound is sound from an umbilical artery or sound from a uterine artery. This can be determined from the position of the sound sensor and/or from the heart rate and other characteristics of the sound from the blood flow. It may be preferred to adjust one or more parameters of the further signal processing depending on whether the recorded sound emanates from an umbilical artery or from a uterine artery.

The system may be arranged to compare the first signal parameter to a threshold and trigger an alarm event in case the first signal parameter exceeds the threshold, such as an alarm event comprising at least one of: a visual alarm signal, an acoustic alarm signal, and a tactile alarm signal. The system may be arranged to alarm the pregnant woman, and/or medical staff, and thus the alarm may be communicated to several locations, e.g. wirelessly such as via the internet and/or a mobile phone net of the like.

The at least one sound sensor may comprise at least a microphone and/or an accelerometer. Preferably, the at least one sound sensor has a noise floor equivalent to a Sound Pressure Level of less than 40 dB re. 20 µPa, such as a Sound Pressure Level of less than 30 dB re. 20 µPa. This is found suitable to obtain a reliable detection of the weak artery sounds.

The system may comprise a plurality of sound sensors functionally connected to the processing unit, wherein the plurality of sound sensors are arranged for respective positions on the abdomen. This allows the system to function at different positions of the fetus in the uterus. Especially, the processing unit may be arranged to process signals received from the plurality of sound sensors and to calculate a parameter, e.g. a measure of signal-to-noise ratio, for each sound sensor, and to select which of the plurality of sound sensors to use for monitoring, based on said calculated parameter. Thus, the sound sensor delivering the best signal can be selected for the actual monitoring. Especially, the processing unit may be arranged to re-calculate the parameter for each sound sensor, so as to allow an updated selection of which of the plurality of sound sensors to use for monitoring. Hereby, the system will automatically adapt to e.g. different positions of the fetus, a damaged microphone or the like.

In one embodiment, the system comprises at least one microphone arranged to detect environmental sound near the sound sensor, wherein the at least one microphone is functionally connected to the processing unit, and wherein the processing unit is arranged to cancel influence from environmental noise in the signal from the sound sensor based on an input received from the at least one microphone. This allows the monitoring system to work in noisy environments. The processing unit may be arranged to cancel influence from environmental noise in the signal from the sound sensor by means of a noise cancellation algorithm comprising Wiener-filtering. Additional or alternative noise calculation algorithm such as known in the art may be selected. In case more sound sensors are used, it may be preferred that each sound sensor has it respective microphone to capture environmental noise placed in close proximity to each sound sensor, in order to provide the best possible input to the noise cancellation algorithm.

The first processing algorithm may be arranged to at least high-pass filter the first signal and generate a high-pass filtered first signal accordingly, wherein the high-pass filter has a cut-off frequency within the range 50-200 Hz, such as within 50-150 Hz, such as 100-200 Hz. Such initial high-pass filtering of the signal received from the sound sensor serves to provide a clean signal for further processing. It is to be understood that the exact cut-off frequency of the high-pass filter may be selected within the given interval without significant different result, the same applied to the slope of the high-pass filter which may be selected in dependence of the used sound sensor and other factors. It may in addition be preferred to low-pass filter the first signal, and thus provide a band-pass filter, as already mentioned.

In a second aspect, the invention provides a method for monitoring a fetus in a pregnant woman and/or for monitoring the maternal risk state in pregnancies complicated by such as pre-eclampsia or hypertensive disorders. The method comprises detecting a vascular sound from a uterine artery or from an umbilical artery of a fetus present in the pregnant woman's uterus by means of at least one sound sensor arranged on the skin of the abdominal area, the at least one sound sensor being arranged in a portable or wearable unit arranged for being carried by the pregnant woman, generating a first signal according to the detected vascular sound, executing a first processing algorithm on the first signal so as to extract at least a first signal parameter accordingly, and communicating the at least first signal parameter.

The first and second aspects may each be combined with any of the other aspects. These and other aspects of the invention will be apparent from and elucidated with reference to the embodiments described hereinafter.

BRIEF DESCRIPTION OF THE FIGURES

Embodiments of the invention will be described in more detail in the following with regard to the accompanying figures. The figures show one way of implementing the present invention and is not to be construed as being limiting to other possible embodiments falling within the scope of the attached claim set.

DETAILED DESCRIPTION OF AN EMBODIMENT

Figure 1:
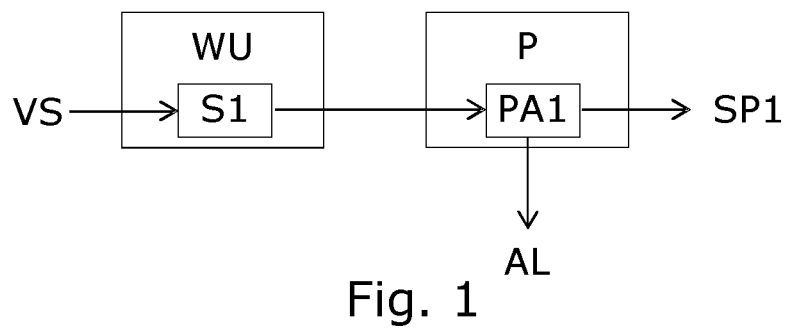
FIG. 1 shows a block diagram of an embodiment.

FIG. 1 shows a simple block diagram of an embodiment. A vascular sound signal VS from an umbilical artery or a uterine artery is detected by a sound sensor S1 placed on the skin of the abdominal area of the pregnant woman. The sound sensor S1 preferably comprises a microphone arranged to sense low amplitude signals ranging from 50-5000 Hz, or at least up to 1000 Hz, preferably up to 2000 Hz. A requirement for the sound sensor is low inherent (thermal) noise and a high sensitivity in order to record the weak vascular sounds. A noise floor below 30 dB SPL is preferred.

The sound sensor S1 is placed within a portable unit here shown as a wearable unit WU to be worn by the pregnant woman, and which is preferably arranged with some kind of attachment or fixing means so as to be able to maintain the sound sensor S1 in the correct position during the pregnant woman performing normal daily activities or also during birth. The wearable unit WU may include various types of fixing means serving this purpose such as straps, belts, plaster etc. Especially, the wearable unit WU may comprise an adhesive patch with the sound sensor S1 arranged within the patch so as to provide a watertight cavity for the sound sensor S1 and necessary battery and electronic circuits connected to the sound sensor S1 in order to provide an electric output signal in accordance with the sensed sound. The system might also comprise several patches as described above, where each patch contains a sound sensor for recording of the sound signal from its position on the abdominal wall. The patches may be wired together to the wearable unit. This or these electric output signal(s) is/are applied, wired or wirelessly, to a processing unit P which executes a first processing algorithm PA1.

The processing algorithm PA1 preferably operates on a time frame of the sound signal from the sound sensor S1, e.g. frames of 1-60 seconds, such as 5-10 seconds, and calculates a first signal parameter SP1 indicative of the umbilical and/or uterine arterial blood flow, such as calculating a measure of the Pulsatility Index (PI), possibly more signal parameters may be calculated. Further, the processing unit P can be arranged to evaluate the first signal parameter SP1 with a tabulated threshold value, and communicate an alarm signal AL in case the normal threshold value is exceeded. The processing unit may also be able to communicate the first signal parameter SP1 to external units. Especially, the first signal parameter SP1 may be communicated to an external server or the like. E.g. the first signal parameter SP1 may be presented in a graph at a display for medical staff at the hospital where the first signal parameter is presented versus time for e.g. one hour, one day or several days, so as to allow the medical staff to monitor the health state of the fetus and diagnose the pregnant woman.

Figure 2:
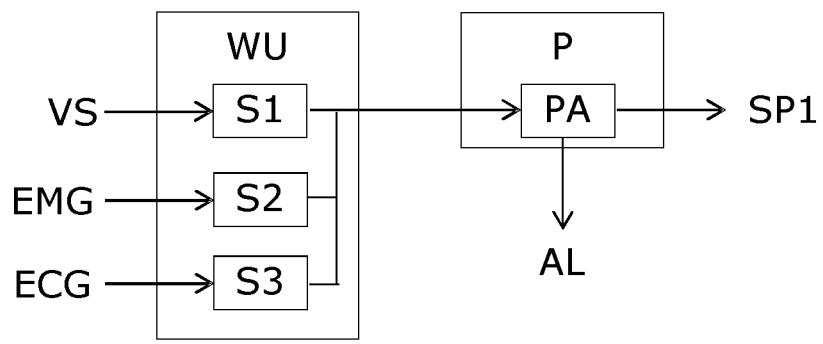
FIG. 2 shows a block diagram of another embodiment.

FIG. 2 shows another embodiment where the element described in relation to FIG. 1 are also present, but in this embodiment, the wearable unit WU also comprises a sensor S2 arranged to sense an electromyographic EMG signal from the uterus, and a sensor S3 arranged to sense an electrocardiographic signal from the fetus inside the uterus. Both of these sensors S2, S3 are also placed on the skin of the abdomen of the pregnant woman. Time signals from all of the three different sensors S1, S2, S3 are applied to the processing unit P which executes a processing algorithm PA handling data from all three sensors S1, S2, S3 and generates a set of signal parameters SP, preferably at least one for each sensor S1, S2, S3, in response to the time signals from the sensors S1, S2, S3. In practice different algorithms are run for each of the sensors S1, S2, S3, and thus different signal parameters SP are derived accordingly. The processing unit P may be arranged to take into account all signal parameters P and perform a combined evaluation and possibly generate an alarm signal AL in case an abnormal status is detected.

Figure 3:
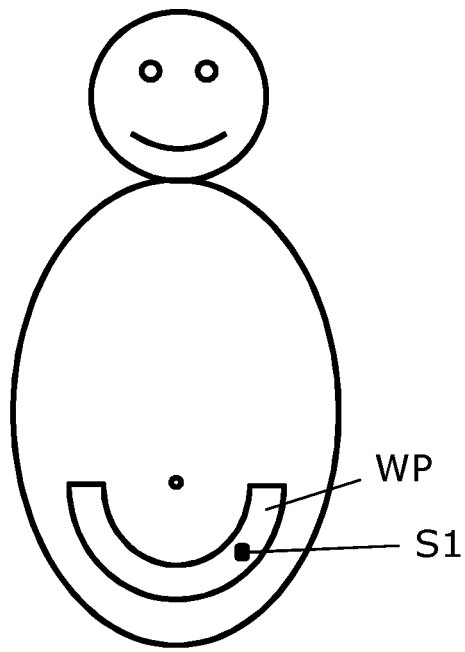
FIG. 3 shows an example of a patch with a built-in sound sensor to be placed on the abdomen of the pregnant woman.

FIG. 3 shows a sketch of a pregnant woman and a wearable unit WU implemented as an adhesive path which is semi-circular or C-shaped in order to fit a lower abdominal area, e.g. the patch may be positioned about 10-15 cm below the umbilicus with direction towards the pelvic bone for optimal sound capturing. A sound sensor S1 is indicated within the patch. It is to be understood that preferably also a battery and the necessary electronic circuit related to the sound sensor S1 are placed within the patch. However, in simple versions, the sound sensor S1 may be connected to the external circuits via a wire, such as a wire connected to other parts of the wearable unit WU, e.g. a small portable device suited for being placed in a belt, a strap, or in a pocket. The patch may be delivered together with a guidance, such as including a template that allows the pregnant woman to position and mount the adhesive patch herself.

Figure 4:
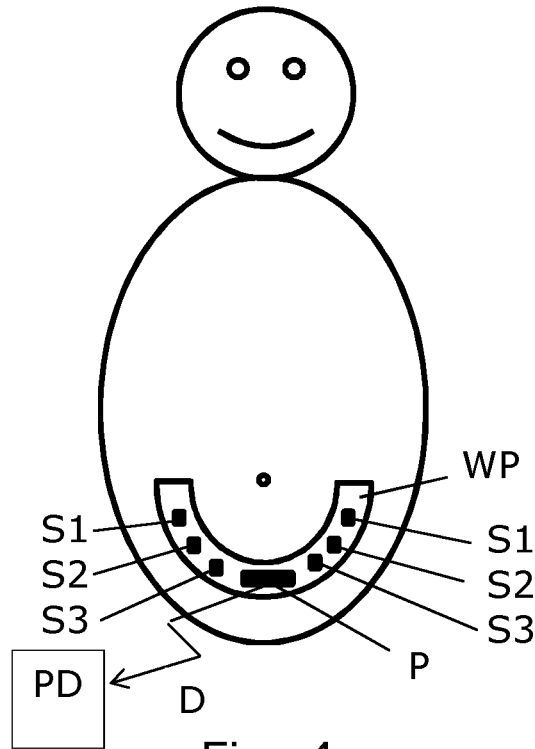
FIG. 4 shows an example of another patch with built-in sound sensors as well as EMG and ECG sensors.

FIG. 4 shows another version of the patch of FIG. 3. Here, two sound sensors S1, two EMG sensors S2, and two fetus ECG sensors S3 are placed within the patch of the portable or wearable unit WU. The two sensors of each type are placed at different positions so as to increase the chance of successfully retrieve the desired signals, compared to only one sensor. Further, the processing unit P connected to the sensors S1, S2, S3, including a battery, is also placed within the patch of the wearable unit WU. The processing unit P is arranged to wirelessly communicate a data signal D to a portable device PD, e.g. a mobile phone, a smart phone device, or the like, by means of a short-range wireless communication link such as Bluetooth. The data signal D may include one or more signal parameters extracted based on the signals from the sensors S1, S2, S3.

The portable device PD, e.g. a smart phone, can then be used to process the data signal D and to communicate the result—e.g. using text and graphics on the display of the smart phone, such as "All OK" or "Please contact the clinic for a check". In case serious problems are detected, an acoustic or visual alarm may be communicated to the pregnant woman, utilizing the audio and video capabilities of the smart phone. Further, the smart phone may run an application which automatically communicates parts of or all of the performed results to the hospital, so as to allow a medical doctor to further analyse the results.

In one specific embodiment, the sound sensor in the form of one or more microphones or accelerometer are positioned within an adhesive patch, with the processing unit arranged also within this patch. This processing unit may perform all processing required, or it may merely serve the purpose of receiving the microphone signals and transmitting it further in a wireless signal, e.g. to a mobile phone or the like which has the processing power and is programmed to perform further processing. In case the processing unit within the patch includes further processing tasks, the processing unit may in wireless form transmit only in case an abnormal situation is detected, e.g. to a mobile phone or the like. Thus, the mobile phone may in such case be programmed to display: "Please contact hospital or doctor". Alternatively, the processing unit within the patch may transmit further detailed data, e.g. a calculated PI, e.g. at regular intervals. Such embodiment can be used for home monitoring, when the pregnant woman is hospitalized, or during the birth phase. In addition to the uterine artery or umbilical artery sound input, the patch may include also an EMG sensor to monitor for (too early) birth pangs, and an ECG sensor to monitor the pulse rate of the fetus. Hereby, the system will be suited both for home monitoring and also as monitoring unit to be used in birth phase.

Figure 5:
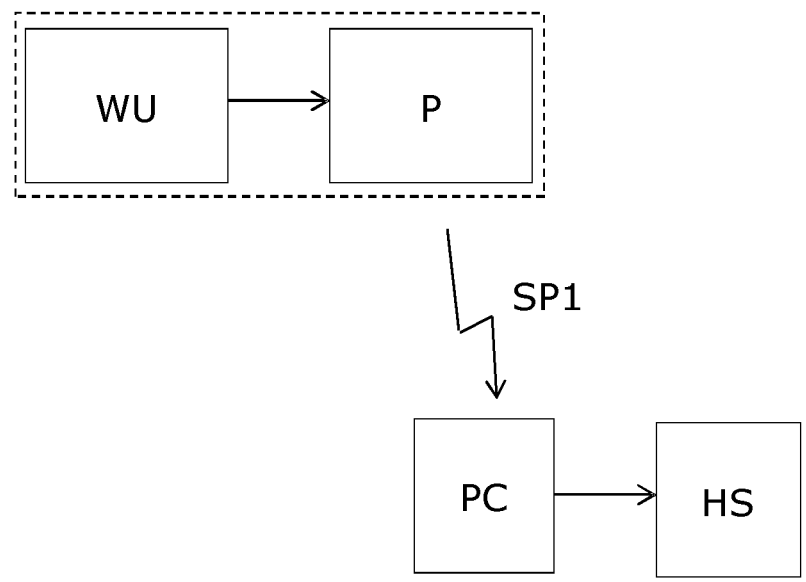
FIG. 5 shows a block diagram of a telehealth care embodiment.

FIG. 5 shows a block diagram of a tele healthcare system embodiment, where a system including a wearable unit WU with a sound sensor and a processing unit P communicate a first signal parameter SP1, e.g. a PI value, wirelessly to a Personal Computer PC in the pregnant woman's home, and the Personal Computer PC is then connected and supplied with software arranged to transmit data to a hospital server HS via the internet, such as at regular intervals, e.g. once a day etc. Hereby, the pregnant woman can live a normal life, but still be monitored at a regular basis by a medical staff which can receive relevant information regarding the monitored umbilical and/or uterine arterial blood flow. Further, the hospital server HS may run software monitoring the incoming data according to a predetermined evaluation algorithm and generates alarm signal in response, if abnormalities are detected.

Figure 6:
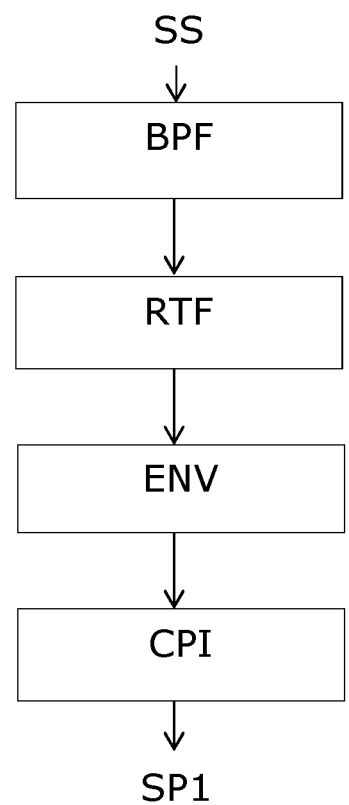
FIG. 6 shows preferred steps of the processing of the sound signal to derive a meaningful signal parameter indicative of the arterial blood flow.

FIG. 6 shows a block diagram of a preferred signal processing to be applied to sound signal SS captured by the sound sensor in order to derive one or more signal parameters indicative of the umbilical and/or uterine arterial blood flow. In a first step, the sound signal SS is preferably band-pass filtered in a band-pass filter BPF with a band-pass frequency range of 50-5000 Hz or a more narrow filter, e.g. down to such as 100-1500 Hz or even 200-800 Hz, e.g. implemented as a Chebychev type-2, with a pass-band ripple of 1 dB, and with a stop-band attenuation of more than 40 dB. Next, the signal is rectified RTF, and next an envelope ENV of the rectified and filtered signal is extracted. Especially, the envelope may be obtained by low-pass filtering the rectified signal, e.g. using a Chebychev type-2 filter, with a cut-off frequency of 1-10 Hz, such as 4-8 Hz, e.g. 6 Hz, with a pass-band ripple of such as 2 dB, and a stop band attenuation of more than 40 dB. From the resulting envelope, several parameters can be extracted. E.g. the Pulsatility Index PI is one (calculated as peak/bottom ratios), a rise-time and a decay-time of the pulses are other signal parameters of interest. There seems to be "dicrotic notches" on the falling edges of the envelope, which may also be used in further investigations.

It is to be understood that several additional or alternative signal processing algorithms may be performed, and there are several parameters to vary: frequencies of the band-pass filter, frequency of the low-pass filter, and also the frequency distribution and changes therein during the pulses, can be of interest.

Figure 7A:
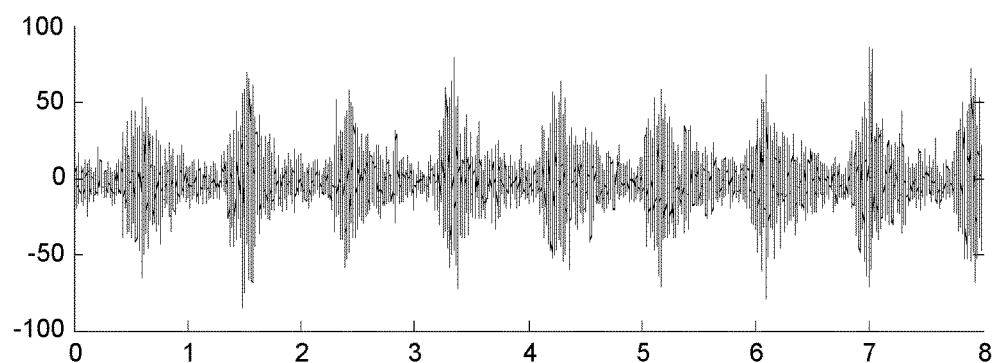
FIGS. 7*a*-7*d* illustrate different steps of the preferred processing steps of FIG. 6 by graphs showing time data at different stages of the processing.
Figure 7B:
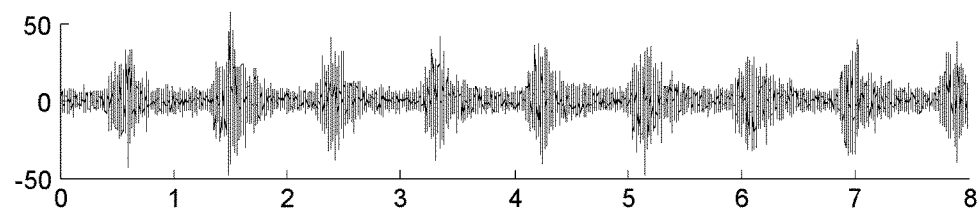
Figure 7C:
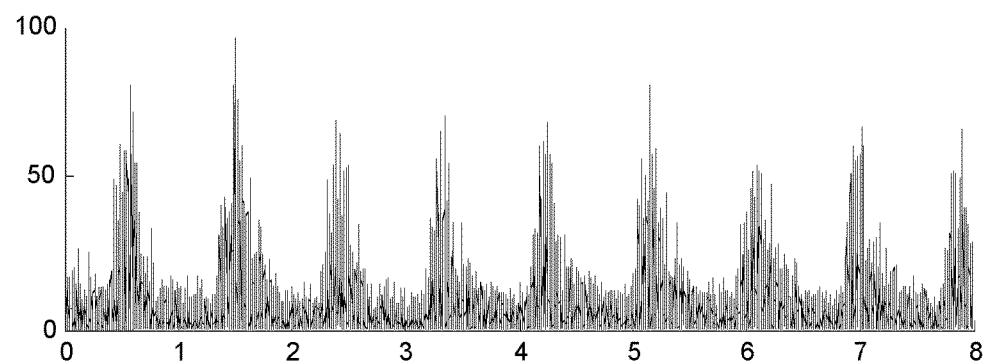
Figure 7D:
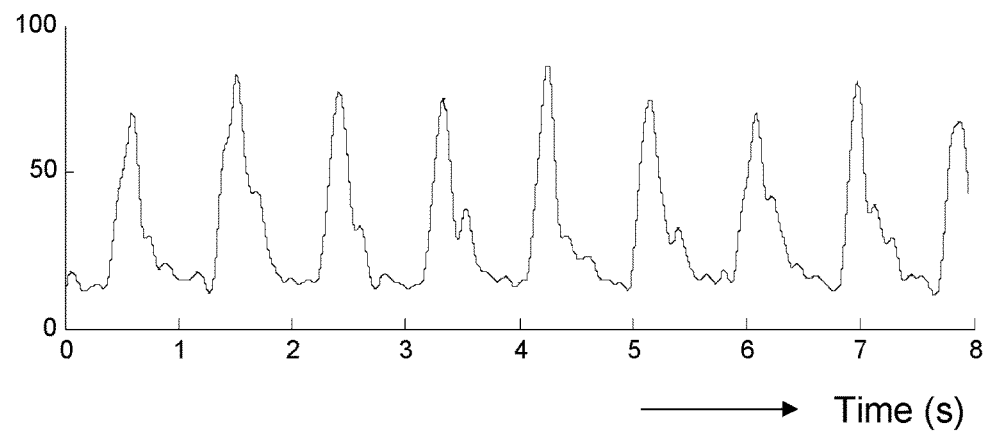

FIGS. 7a-7d show examples of an 8 second sound signal at various steps of a preferred signal processing algorithm just described. FIG. 7a shows the raw sound signal picked up at the abdominal skin of a pregnant woman, and the signal is presented as amplitude versus time. The pulse rate, slightly above 60 beats per minute, is clearly seen. Altogether, the sound of the umbilical or uterine arteries reflects the state of the maternal blood supply to the placenta, the blood flow between the placenta and the fetus, as well as events in the fetal cardiac cycle, i.e. the deceleration of blood, turbulence of the blood flow and the closing of the fetal heart valves. FIG. 7b shows the signal after band-pass filtering with a 200-800 Hz band-pass filter. FIG. 7c shows the band-pass filtered signal after rectification, and finally FIG. 7d shows the signal envelope resulting from a 6 Hz low pass filtering. The envelope can be used, among others, to derive the PI.

To sum up, the invention provides a system for monitoring a fetus in a pregnant woman, and/or the maternal health risk for pregnancies complicated by such as pre-eclampsia, and hypertensive disorders. The system comprises a portable or wearable unit that can be worn by the pregnant woman, preferably so as to allow monitoring during daily life (home monitoring), e.g. in the form of an adhesive patch. The portable unit has a sound sensor, e.g. a microphone or accelerometer, to be positioned on the skin of the abdominal area of the pregnant woman so as to detect a vascular sound from the uterine arteries and/or umbilical arteries of the fetus. The sound sensor is functionally connected to a processing unit which executes a processing algorithm on the captured vascular sound and extracts a signal parameter accordingly, e.g. the Pulsatility Index. The processing unit then communicates the signal parameter, e.g. using an audio signal, a visual display or by means of a wired or a wireless data signal. Some embodiments include one or more additional sensors, such as a sensor for detecting fetal electrocardiographic signals, and/or a sensor for detecting uterus electromyographic activity. Especially, the sound sensor and such additional sensor(s) may be arranged within one adhesive patch.

Although the present invention has been described in connection with the specified embodiments, it should not be construed as being in any way limited to the presented examples. The scope of the present invention is set out by the accompanying claim set. In the context of the claims, the terms "comprising" or "comprises" do not exclude other possible elements or steps. Also, the mentioning of references such as "a" or "an" etc. should not be construed as excluding a plurality. The use of reference signs in the claims with respect to elements indicated in the figures shall also not be construed as limiting the scope of the invention. Furthermore, individual features mentioned in different claims, may possibly be advantageously combined, and the mentioning of these features in different claims does not exclude that a combination of features is not possible and advantageous.

The invention claimed is:

1. A method for monitoring a pregnant woman or a fetus in a pregnant woman, said method comprising:
   arranging a sound sensor on an abdomen of the pregnant woman;
   capturing sound in the frequency range of 50-5000 Hz by the sound sensor;
   detecting a vascular sound from a uterine artery or an umbilical artery of a fetus present in the pregnant woman's uterus using the captured sound in the frequency range of 50-5000 Hz from the sound sensor;
   processing the detected vascular sound to represent a state of the maternal blood supply to a placenta and/or blood flow between the placenta and the fetus.

2. The method according to claim 1, wherein the detected vascular sound is processed in a frequency range of 50-4000 Hz.

3. The method according to claim 2, wherein the frequency range in which the detected vascular sound is processed is 50-3000 Hz.

4. The method according to claim 2, wherein the frequency range in which the detected vascular sound is processed is 80-2000 Hz.

5. The method according to claim 2, wherein the frequency range in which the detected vascular sound is processed is 100-1000 Hz.

6. The method according to claim 2, wherein the frequency range in which the detected vascular sound is processed is 200-800 Hz.

7. The method according to claim 1, wherein said arranging comprises arranging a portable or wearable unit comprising the sound sensor on the abdomen of the pregnant woman.

8. The method according to claim 7, further comprising performing detections of vascular sound over a period of hours, during which the portable or wearable unit is worn by the pregnant woman.

9. The method according to claim 1, wherein the processing comprises identifying deceleration of blood and/or turbulence of blood flow.

10. The method according to claim 1, further comprising detecting a hypertensive disorder based on the processing of the detected vascular sound.

11. The method according to claim 1, wherein the processing comprises executing a processing algorithm on a signal according to the detected vascular sound so as to extract at least a signal parameter accordingly to represent the state of the maternal blood supply to placenta and/or blood flow between the placenta and the fetus.

12. A system for monitoring a pregnant woman or a fetus in a pregnant woman, said device comprising:
   a sound sensor configured to be arranged on an abdomen of the pregnant woman and configured to capture sound in the frequency range 50-5000 Hz and to detect a vascular sound from a uterine artery or an umbilical artery of a fetus present in the pregnant woman's uterus using the captured sound in the frequency range 50-5000 Hz from the sound sensor;
   a processing unit functionally connected to the sound sensor, said processing unit being configured to execute a processing algorithm on the detected vascular sound to extract a signal parameter accordingly to represent a state of the maternal blood supply to a placenta and/or blood flow between the placenta and the fetus.

13. The system according to claim 12, wherein the processing unit is configured to process detected vascular sound in a frequency range of 50-4000 Hz.

14. The system according to claim 13, wherein the frequency range in which the detected vascular sound is processed is 50-3000 Hz.

15. The system according to claim 13, wherein the frequency range in which the detected vascular sound is processed is 80-2000 Hz.

16. The system according to claim 13, wherein the frequency range in which the detected vascular sound is processed is 100-1000 Hz.

17. The system according to claim 13, wherein the frequency range in which the detected vascular sound is processed is 200-800 Hz.

18. The system according to claim 12, further comprising a portable or wearable unit in which the sound sensor is arranged, wherein the portable or wearable unit is configured to be worn by the pregnant woman.

* * * * *